United States Patent [19]

Oberst et al.

[11] Patent Number: 5,350,672

[45] Date of Patent: Sep. 27, 1994

[54] SPECIFIC DNA PRIMERS AND METHOD TO USE SAME DETECT EPERYTHROZOON SUIS

[75] Inventors: Richard D. Oberst; Sharon M. Gwaltney, both of Manhattan; Michael P. Hays, Leonardville, all of Kans.

[73] Assignee: Kansas State University Research Foundation, Manhattan, Kans.

[21] Appl. No.: 9,261

[22] Filed: Jan. 22, 1993

[51] Int. Cl.$^5$ .............................................. C12Q 1/68
[52] U.S. Cl. .................................... 435/6; 536/24.3; 536/24.32; 435/252.1
[58] Field of Search ................ 435/6, 91.2; 536/24.32, 536/24.3

[56] References Cited

PUBLICATIONS

Ludwig et al., International J. Systematic Bacteriology, 42(1): 161–167, Jan. 1992.

Beaucage, S. L., et al., "Deoxynucleoside Phosphoramidites–A New Class of Key Intermediates for Deoxypolynucleotide Synthesis," Tetrahedron Letters 22:1859–1862 (1981).

Gwaltney, Sharon M., et al., "Detection of Eperythrozoon suis using the polymerase chain reaction," J. Vet. Diagn. Invest. 5:40–46 (1993).

Hall, S. M., et al., "Isolation of Infective and Non–infective Eperythrozoon suis Bodies From the Whole Blood of Infected Swine, " Vet. Rec. 123:651 (1988).

Hsu, Frank S., et al., "Evaluation of an Ezyme–linked Immunosorbent Assay for Detection of Eperythrozoon suis Antibodies in Swine," Am. J. Vet. Res. 53:352–354 (1992).

Mullis, Kary B., "Specific Synthesis of DNA in vitro via a Polymerase–Catalyzed Chain Reaction," Methods in Enzymology 55:335–350 (1987).

Oberst, R. D., et al., "Recombinant DNA Probe Detecting Eperythrozoon suis in Swine Blood," Am. J. Vet. Res. 51:1760–1764 (1990).

Oberst, R. D., et al., "Detection of Eperythrozoon suis DNA from Swine Blood by Whole Organism DNA Hybridizations," Vet. Microbiol. 24:127–134 (1990).

Ou, Chin-Yih, et al., "DNA Amplification for Direct Detection of HIV-1 DNA of Peripheral Blood Mononuclear Cells," Science 239:295–297 (1988).

Panaccio, et al., "PCR Based Diagnosis in the Presence of 8% (v/v) Blood," Nucleic Acids Research 19:1151 (1991).

Saiki, Randall K., "Primer–Directed Enzymatic Amplification of DNA With a Thermostable DNA Polymerase," Science 239:487–491 (1988).

Sanger, F., et al., "DNA Sequencing With Chain-Terminating Inhibitors," Proc. Natl. Acad. Sci. USA 74:5463–5467 (1977).

Smith, A. R., et al., "An Indirect Hemagglutination Test for the Diagnosis of Eperythrozoon suis Infected in Swine," Am. J. Vet. Res. 36:1319–1321 (1975).

Southern, E. M., "Detection of Specific Sequences Among DNA Fragments Separated by Gel Electrophoresis," J. Mol. Biol. 98:503–517 (1975).

Welsh, J., et al., "Fingerprinting Genomes Using PCR with Arbitrary Primers," Nucleic Acids Res. 18:7213–7218 (1990).

Zoig, J. W., et al., "High Salt Lysates: A Simple Method to Store Blood Samples Without Refrigeration for Subsequent Use With DNA Probes," Am. J. Trop. Med. Hyg. 39(1):33–40 (1988).

Primary Examiner—Margaret Parr
Assistant Examiner—Scott W. Houtteman
Attorney, Agent, or Firm—Tilton, Fallon, Lungmus & Chestnut

[57] ABSTRACT

The use of E. suis specific primers in PCR with DNA from swine blood increases the sensitivity of current DNA hybridization protocols for determining whether swine are infected with E. suis prior to the development of any clinical symptoms. The present invention provides these E. suis primers and a method to use these primers in a PCR protocol to provide a highly sensitive diagnostic assay for early signs of an E. suis infection.

4 Claims, 1 Drawing Sheet

Fig. 1

5' TCTTCAACTCTTCCTATGGATCTAGAAAGAGTATGGCTGACACAGCAGTGAAAACTGCTAAGT
CAGGTTACATGACTAGACATGAAAAACTTGTGGATGCTTCACAAGAAGTAGTTAGATCCATAGACTGT
AATCCTAAGAAGGGAGTCTTAATAAGAGCTATTAAGGCTGAGGGAAGTGACAGTATGGTTAAGAC
TCTTGAAGAGAGACTTAGATATAGATACTTACTCCTAAGATAGTGCCGTTTAAGGACATTGTATGTCCTCAAACAGGAGAAG
TACTGTGTGCTGAAGGAGAATACTTACTTGTGAACAAAATAGCTAAGAAAATACAAGATCTTGGATTCG
AAGAAGTAGAAGTGAGAGGAGCATTTACTTGTGAACAAAAACCATGGTGTTTGTCAAAATGT
TTCGGTTACGACCTTAAGACTAAGAAAACCAGTAAGGTCGGAACTGCTGTCGGAATAATTGCAGC
TCAATCAATTGGTGAGCCTGCAACAACTTACCATAG 3' Sequence Id. no. 3

5' CTCATGGTAAGTTGTGTTGCAGGCTCACCAATTGATTGAGCTGCAATTATTCCGACAGCA
GTTCCGACCTTAACTGGTTTCTTAGTCTTAAGGTCGTAACCGAAACATTTTGACAAACA
CCACATGGTTTTGTTCACAAGTAAATGCTCCTCTCACTTCTTCTTCGAATCCAAGA
TCTTGTATTTCTTAGCTATCTTAGGAGTAAGTATTCTCCTTCAGCACACAGTACTTCTC
CTGTTTGAGGACATACAATGTCCTAAACGCACACATCTATATCTAAGTCTCTCTTCAAGAG
TCTTAACCATACTGTCACTTCCCTCAGCCTTAATAGCTCTTATTAAGACTCCCTTCTTAG
GATTACAGTCTATGGATCTAACTACTACTTCTTGTGAAGCATCCACAAGTTTTCTAGTCA
TGTAACCTGACTTAGCAGTTTTCACTGCTGTGTCAGCCATACTCTTTCTAGATCCATAGG
AAGAGTTGAAGA 3' Sequence Id. no. 4

SPECIFIC DNA PRIMERS AND METHOD TO USE SAME DETECT *EPERYTHROZOON SUIS*

FIELD OF THE INVENTION

The field of this invention is the detection of the organism *Eperythrozoon suis*. More particularly, the invention is concerned with the identification of *E. suis* DNA sequences that can be used to probe for *E. suis* genomic DNA. This invention provides a specific DNA probe and describes its use in a primer directed amplification assay for *E. suis*.

BACKGROUND OF THE INVENTION

Detection of DNA in specimens comprising body fluids of tissues can be difficult because of the small quantity of DNA present or because of the presence in the specimen of other interfering materials, including DNA from a different source. These limitations may be overcome by employing an analytic method referred to as the polymerase chain reaction (PCR) technique. By this technique, selective enrichment of a specific DNA sequence can be achieved by exponential amplification of the target sequence. Mullis, et al., *Meth Enzymol.*, 155, 335 (1987).

To facilitate PCR amplification, pairs of oligonucleotide primers may be employed as described in U.S. Pat. No. 4,683,202 (hereby incorporated by reference). The primers are designated to hybridize with sequences that flank the target DNA. Following in vitro amplification, the amplified target sequence is detected by a hybridizing probe. For example this analytical procedure has been used for the direct detection of HIV-1 as described by Ou, et al., *Science*, 238:295-97 (1988). The amplification cycles are facilitated by using a polymerase which is thermally stable in incubations up to 95° C. as described by Saiki, et al., *Science*, 239:487-91 (1988).

*E. suis* is an extracellular red blood cell parasite that causes icteroanemia in acutely ill pigs and a variety of syndromes in chronically infected pigs. Current techniques to detect *E. suis* infection are limited by the variability of parasitemia and the antibody response in the infected animal. In particular, diagnosis of eperythrozoonosis is complicated by lack of readily identifiable parasitemia in latent and chronic infections, rapid loss of parasitemia at the time of onset of clinical signs in acutely ill pigs and the lack of sensitive and specific laboratory tests for the organism.

Serological tests for eperythrozoonosis include an indirect hemagglutination test (IHA), Smith et al., *J. Am. Vet. Med. Assoc.*, 36:1319-20 (1975) and an enzyme linked immunosorbent assay (ELISA), Hsu et al., *J. Am. Vet. Med. Assoc.*, 53:352-54 (1992). The ELISA test provided superior results to the IHA test in sensitivity; but, both of these tests share limitations because of the nature of the antibody response to *E. suis* in pigs. Young pigs, i.e. less than twelve weeks, and boars have low titers to the organism and the antibody titers tend to decline rapidly in chronically infected individuals. Because of this variability in the antibody response, the standard ELISA and IHA tests are more useful as tests to screen herds for *E. suis* but have limited value in diagnosis of acute eperythrozoonosis.

Genetic approaches to diagnosing eperythrozoonosis have been reported. Oberst, et al., *Am. Vet. Res.*, 51:1760-64 (1990 hereby incorporated by reference). A recombinant DNA probe to *E. suis* was used to detect *E. suis* DNA extracted from the blood of experimentally infected, splenectomized pigs. The DNA probe (KSU-2) was able to detect infection seven days post infection, which corresponds with the appearance of clinical signs and detectable parasitemia on blood smears. Although this probe is specific for detecting *E. suis* in acutely ill pigs, it was unable to detect infections during the prepatent period (i.e. days 1 through 6) before the pigs become clinically ill. As such a need existed for an efficient diagnostic test which can be used to detect early infection with *E. suis* so that steps can be taken prior to the outbreak of clinical symptoms.

SUMMARY OF THE INVENTION

The present invention provides a method for detecting a portion of the genome of *E. suis*. This method uses dual primers for amplification and detection of significant segments of *E. suis*. In particular a method of identifying early *E. suis* infection in pigs by primer directed amplification is provided. In this method a sample of blood DNA from a pig is obtained and prepared for amplification. The treated sample is amplified with dual primers consisting of the following two single strand oligonucleotides: TCTTCAACTCTTCCTATGGA Sequence Id. no. 1 and CTCATGGTAAGTTGTGTTGC Sequence Id. no. 2, and following amplification, an early *E. suis* infection can be detected by hybridizing with a cloned 492 base pair fragment (sequence Id. no. 3) or KSU-2 DNA probe and detecting the hybridized probe wherein A is adenosine, T is thymidine, G is guanosine, and C is cytosine, the sequence being in the 5' to 3' orientation.

Additionally this invention provides synthetic oligonucleotides useful in detecting the early *E. suis* infection represented by the DNA sequence TCTTCAACTCTTCCTATGGA Sequence Id. no. 1 and the DNA sequence CTCATGGTAAGTTGTGTTGC Sequence Id. no. 2, wherein A is adenosine, T is thymidine, G is guanosine, and C is cytosine, the sequence being in the 5' to 3' orientation. Additionally a primer directed amplification product of KSU-2 is provided having the nucleic acid sequence:

```
5'TCTTCAACTCTTCCTATGGATCTAGAAAGAGTATGGCTGACACAGCAGTGAAAACTGCTAAGT           (Sequence Id. no. 3)
CAGGTTACATGACTAGAAAACTTGTGGATGCTTCACAAGAAGTAGTAGTTAGATCCATAGACTGT
AATCCTAAGAAGGGAGTCTTAATAAGAGCTATTAAGGCTGAGGGAAGTGACAGTATGGTTAAGAC
TCTTGAAGAGAGACTTAGATATAGATGTGCGTTTAAGGACATTGTATGTCCTCAAACAGGAGAAG
TACTGTGTGCTGAAGGAGAATACTTACTCCTAAGATAGCTAAGAAAATACAAGATCTTGGATTCG
AAGAAGTAGAAGTGAGAGGAGCATTTACTTGTGAACAAAAACCATGTGGTGTTTGTCAAAAATGT
TTCGGTTACGACCTTAAGACTAAGAAACCAGTTAAGGTCGGAACTGCTGTCGGAATAATTGCAGC
TCAATCAATTGGTGAGCCTGCAACACAACTTACCATGAG 3'

5'CTCATGGTAAGTTGTGTTGCAGGCTCACCAATTGATTGAGCTGCAATTATTCCGACAGCA           (Sequence Id. no 4)
GTTCCGACCTTAACTGGTTTCTTAGTCTTAAGGTCGTAACCGAAACATTTTTGACAAACA
CCACATGGTTTTTGTTCACAAGTAAATGCTCCTCTCACTTCTACTTCTTCGAATCCAAGA
TCTTGTATTTTCTTAGCTATCTTAGGAGTAAGTATTCTCCTTCAGCACACAGTACTTCTC
CTGTTTGAGGACATACAATGTCCTTAAACGCACATCTATATCTAAGTCTCTCTTCAAGAG
```

-continued

TCTTAACCATACTGTCACTTCCCTCAGCCTTAATAGCTCTTATTAAGACTCCCTTCTTAG
GATTACAGTCTATGGATCTAACTACTACTTCTTGTGAAGCATCCACAAGTTTTCTAGTCA
TGTAACCTGACTTAGCAGTTTTCACTGCTGTGTCAGCCATACTCTTTCTAGATCCATAGG
AAGAGTTGAAGA 3'.

The twenty oligonucleotide primers are underlined and in bold face print.

BRIEF DESCRIPTION OF THE DRAWINGS

FIG. 1 shows the DNA sequence for a 492 base pair amplification product set out as sequence Id. nos. 3 and 4.

DETAILED DESCRIPTION OF THE INVENTION

The method of this invention uses synthetic oligonucleotide sequences as primers. These sequences can be prepared by well known chemical procedures, and commercially available DNA synthesizers can also be used. For example, the required sequence can be prepared by the synthesis method described by Beaucage, et al., Tetrahedron letters, 22:1859-62 (1981). Another method for the synthesis of oligonucleotide on solid support is described in U.S. Pat. No. 4,458,066. Automated DNA synthesis apparatus can be used such as the DNA synthesizer sold by Applied Biosystems.

Oligonucleotide sequences required for practicing the method of this invention comprise primer sequences and probe sequences or the inversions of the probe sequences. The single strand oligonucleotides are represented by the standard letter abbreviations in which the nucleotides are designated as follows:

A for adenosine,
T for thymidine,
G for guanosine,
C for cytosine.

These strands are represented in a standard 5' to 3' orientation.

Primer Sequences:

Sense strand primer:TCTTCAACTCTTC-CTATGGA Sequence Id. no. 1. Anti-sense stand primer:CTCATGGTAAGTTGTGTTGC Sequence Id. no. 2.

Primer Selection

The primer sequences can be used in the genetic amplification of the E. suis genome. The primers are designed to hybridize with highly conserved regions of the genome. These primers are capable of effectively hybridizing and serving as primers for the thermostable DNA polymerase used in the amplification process. More specifically the primer selection involves the following process. A previously described E. suis specific DNA probe (Oberst, et al., Vet Microbiol, 24:127-34 (1990)) designated KSU-2 was cleaved into two fragments (2.3 and 2.9 Kb in length) using the restriction endonuclease BamHI (Bethesda Research Laboratories, Gaithersburg, Md.). A whole-organism E.suis DNA probe (KSU-2) can be made according to the following procedure. Using a described procedure for identification of E.suis Oberst et al., developed a procedure for the identification of E.suis infected blood samples using radiolabelled whole-organism E.suis DNA as the probe.

Parasite recovery.

Splenectomized pigs were inoculated with E.suis infected whole blood and monitored daily for parasitemias. At peak parasitemia (greater than 90% of erythrocytes infected with E. suis, as determined by microscopic examination of blood smears), whole blood was collected, and E.suis was isolated and purified (Hall et al., Vet. Res., 123:651 (1988)). E.suis infected swine blood was kindly provided by Dr. J. F. Zachery, Department of Pathobiology, College of Veterinary Medicine, University of Illinois, Ill.

Control-negative blood samples were collected from the SPF (Specific Pathogen Free) swine herd maintained by the Department of Veterinary Science at the University of Nebraska-Lincoln, Nebr. All animals tested negative by IHA.

Purification and labelling of purified whole organism DNA.

The whole organism DNA was recovered from purified E. suis by first incubating the organisms for 1 hour at 37° C. in buffer (150 mM NaCl, 5 mM EDTA, and 50 mM Tris-HCl pH 7.5) containing 0.2% Triton X-100 and 10 mg/ml Proteinase K. The E. suis DNA was then extracted with phenol-chloroform and ether (Maniatis et al., 1982), and ethanol precipitated (−20° C. overnight). Aliquots of purified E. suis DNA were labeled to high specific activity ($1 \times 10^8$ dpm $\mu g^{-1}$) with an oligolabelling kit (Pharmacia LKB Biotechnology, Piscataway, N.J. 08855-1327) using [$\alpha$-$^{32}$P]dCTP (3000 Ci $mmol^{-1}$).

Restriction enzyme characterization of purified DNA. Purified E. suis DNA was digested with HindIII and EcoRI as recommended by the manufacturer (BRL Life Technologies, Gaithersburg, Md. 20877). Restriction fragments were resolved on 0.7% agarose gels and stained with ethidium bromide.

DNA sample recovery from whole blood.

To characterize the specificity of the purified, whole-organism DNA, E. suis-infected and noninfected swine blood was collected and the DNA extracted: (1) using phenol-choloform extractions as described above except the organisms were not purified from other blood constitutents, or (2) as described by Zolg et al. Am. J. Trop. Med. Hyg., 39:33-40(1988), utilizing high salt lysates for preserving extracting DNA from blood.

High salt lysates were formulated by placing aliquots of 100 $\mu$l fresh, whole blood into 1.5 ml microcentrifuge tubes and adding 200 $\mu$l sterile water, 100 $\mu$l of 1% N-lauroylsarcosine in 50 mM EDTA pH 8.0, and 100 $\mu$l cesium trifluoroacetate (CsTFA, Pharmacia, Piscataway, N.J. 08855-1327). Proteins were precipitated by adding 0.3 x volumes of a solution containing ethanol:chloroform:isoamyl alcohol (2.:1:0.04), mixing for 5 min and centrifuging at 14 000 x g for 15 min. The supernatant was removed, and the DNA was precipitated with 2 x volumes of 100% ethanol (overnight −20° C).

Extracted DNA was blotted onto membranes according to the manufacturer's instructions (Hybond-N, Amersham, Arlington Heights, Ill. 60005) after being resuspended in 250 $\mu$l of NET buffer (0.15M NaCl, 0.1 mM EDTA, 0.02M Tris-HCl pH 8.0); alternately, the DNA was resolved in 0.7% agarose gels (50 V, 4 hour) with TBE buffer (89 mM Tris-borate, 2.5 mM EDTA, pH 8.0). The DNA was denatured (0.5M NaOH, 1.5M NaCl) for 15 minutes, neutralized (1.5M NaCl, 0.5M Tris-HCl pH 7.2, 1 mM EDTA) for 15 min, and electroblotted from the gels onto membranes for 1 hour at 20° V and 4 hour at 60 V (Trans-Blot, BioRad, Richmond, Calif. 94804). The membranes were air dried, and the DNA was cross-linked on the membrane by ultraviolet illumination for 5 minutes.

DNA hybridizations.

Membranes were prehybridized in 50% deionized formamide, 0.1% sodium dodecyl sulphate (SDS), 10 mg/ml glycine, 0.5 mg/ml denatured salmon sperm DNA, 5xSSC (0.75 M NaCl, 75 mM sodium citrate), and 5 x Denhardt's solution for 1 hour at 42° C.

The E. suis [$^{32}$P] DNA was denatured at 95° C. for 5 minutes, quenched on ice, and then mixed with hybridization buffer (50% deionized formamide, 10% sodium dextran sulfate, 5xSSC, 1xDenhardt's, 0.1% SDS, 0.1 mg/ml denatured salmon sperm DNA). Membranes were hybridized overnight at 42° C., washed twice (2xSSC, 0.1% SDS), then washed once (0.1xSSC, 0.1% SDS) at 42° C. for 30 minutes, dried, and autoradiographed at −70° C. with an intensifying screen.

The specificity of the DNA was determined by oligolabelling the recovered E. suis DNA and hybridizing with purified preparations of E. suis and with infected and uninfected swine blood DNA. The ability of the whole organism [$^{32}$P] DNA probe to distinguish E. suis parasitized blood from uninfected swine blood was demonstrated in slot-blot hybridizations and with blood DNA extracts that were resolved on agarose gels, transferred to membranes, and hybridized.

The initial screenings of unpurified whole bloods for E. suis using Proteinase K digestions and phenol/chloroform extractions resulted in various amounts of aqueous phase that could be collected from above the phenol/chloroform phase. Thus, the volumes of extracted DNA available for probing were highly variable.

The high salt lysate collection and recovery method allowed the same volume of aqueous phase to be obtained from each blood sample. An additional extraction with phenol (saturated with 0.1 M Tris pH 8.0) was added to decrease sample discoloration, and the aqueous phase was ethanol precipitated and resuspended in 250 μof NET buffer prior to blotting. This reduced background on radiographic exposures.

The 2.9 Kb fragment was subcloned into $p$Bluescript (Stratagene Cloning Systems, La Jolla, Calif.) and sequenced using a dideoxy chain termination method. See Sanger et al., Proc. Nat'l. Acad. Sci. USA 74:5463–67 (1977). The sequences were entered in to a primer selection computer software program (NUC IT, Compuright, Washington Grove, Md.) and the two 20-mer primers were selected that would theoretically yield a 492 base pair amplification product. The primers were synthesized using standard phosphoramidite chemical methods (PCR-MATE 391 DNA Synthesizer, Applied Biosystems, Foster City Calif.); lyophilized; resuspended in TE buffer (10 mM Tris-HCl, pH 8.0; 1 mM EDTA); and purified in a SEPHADEX-G50 column (Pharmacia); then the DNA concentration was quantitated ($A_{260}-A_{280}$). Primers were diluted to 20 micromolar in TE buffer and stored at −20° C.

Template and Probe Preparation

The DNA used as the initial template for optimizing the PCR protocol was from KSU-2. The KSU-2 DNA cloned in lambda gt11 was subcloned into $p$Bluescript and propagated in JM109 E. coli. (Oberst et. al., Am. J. Vet. Res. 51:1160–64 (1990 hereby incorporated by reference). The plasmid was excised by EcoRI (Bethesda Research Laboratories, Gaithersburg, Md) and resolved by electrophoresing on 1% low melting temperature agarose gels (30 V, four hours). The fragment (KSU-2) was excised from the gel and fifty nanogram aliquots of KSU-2 DNA were diluted in 20 microliter of TE and stored at −20° C. KSU-2 DNA used as probe was labeled by random priming (Oligolabelling Kit, Pharmacia) using [alpha $^{32}$P]dCTP (3000Ci/mM). (Du Pont/NEN Research Products, Boston, Mass.).

E. suis-infected blood was obtained by inoculating splenectomized pigs with E. suis according to the method described by Oberst et al., Am. J. Vet. Res, 51:1760–1764 (1990). At maximum parasitemia, blood samples were collected in vacuum tubes containing EDTA and stored at −70° C. Purified E. suis organisms (pES) were obtained according to the method described by Hall et al., Vet. Res. 123:651 (1988 hereby incorporated by reference) and stored at −70° C. DNA was extracted from both whole blood and pES using modified quick boil method. Welsh et al., Nucleic Acids Res. 18(24):7213–18 (1990 hereby incorporated by reference). Briefly, 100 microliters of blood or pES were combined with 200 microliters of sterile distilled water and heated to 100° C. for five minutes. The lysate was cooled briefly, phenol-chloroform extracted, and the DNA was ethanol precipitated. See Panaccio et al., Nucleic Acids Res. 19:1151 (1991). The DNA was suspended in 100 microliters of sterile distilled water, quantitated ($A_{260}$-$A_{280}$) and stored at −20° C.

DNA samples isolated from the blood of pigs presumed to be E. suis negative via blood smear analysis and/or IHA testing were used to ensure that any given pig was free of undetected E. suis infection, additional negative controls consisting of DNA from blood of clinically healthy cats were used. The cat blood was collected in EDTA and processed as previously described.

Polymerase Chain Reaction

The DNA amplification protocol used 100 microliter reaction volumes in PCR reactions that were run on an automated DNA thermal cycler (TEMPCYCLER, Coy Corp., Ann Arbor, Mich.). The PCR reagents were used according to the manufacturer's recommendations (Perkin Elmer Cetus Corp.) and the reaction mixtures contained 10 mM Tris-HCl (pH 8.3), 50 mM KCl, 200 micromolar each of the four deoxynucleoside triphosphates, 1 micromolar of each primer, 2.5 mM of $MgCl_2$, 2.5 units of Taq DNA polymerase, and 20 microliters of template. One nanogram of KSU-2 DNA was used as a positive control.

Reaction mixtures were overlaid with one drop of mineral oil, denatured at 94° C. for three minutes, annealed at 37° C. for one minute, and extended at 72° C. for 1 minute for two cycles, followed by 25 cycles of 94° C. for one minute, 37° C. for one minute and 72° C. for 1 minute. Following the last cycle, the mixtures were incubated at 72° C. for five minutes and stored at 4 C.

The modified quick boil method yielded between 3.5 micrograms and 8.5 micrograms of total DNA from 100 microliters of E. suis-infected pig blood, uninfected pig blood, cat blood, or pES. Ten microliters of extract (0.35 to 0.85 micrograms of DNA ) was used as a template for each PCR reaction. Following electrophoresis, all reactions containing DNA extracted from E.

*suis*-infected blood or from pES yielded a band of approximately 500 base pairs, whereas the reactions containing the negative control template DNA showed no amplification product.

Electrophoresis and DNA Hybridizations

The amplification products (25 microliters of each sample) were loaded on to 1% agarose gels and electrophoresed at 100 V for 45 minutes. The gels were stained with ethidium bromide and visualized by ultraviolet illumination. The gels were incubated in denaturation solution (1.5 M NaCl; 0.5 M NaOH) for 30 minutes, then washed in neutralization solutions (1.5 M NaCl; 0.5M Tris-HCl, pH 7.2; 1.0 mM EDTA) for 30 minutes. The DNA was transferred from the gel to nylon membranes by capillary transfer. See Southern, *J. Molec. Bio.* 98:503–07 (1975). Following transfer, the DNA was crosslinked to membranes by ultraviolet illumination (GS GENELINKER, Biorad Laboratories, Richmond, Calif.).

The membranes were placed in prehybridization buffer (50% deionized formamide, 10 mg/ml glycine, 0.1% sodium dodecyl sulfate (SDS), 0.5 mg/ml denatured salmon sperm DNA, 50 mM NaPO$_4$ buffer (pH 6.5), 5X Denhardt's solution, and 6X SSC) and incubated for one hour at 42° C. The prehybridization solution was removed and hybridization solution (50% deionized formamide, 0.1% SDS, 0.1 mg/ml denatured salmon sperm DNA, 20 mM NaPO$_4$ buffer (pH 6.5), 1X Denhardt's solution, 6X SSC) was added. Radiolabelled KSU-2 was denatured at 95° C. for five minutes and added to the hybridization solution. Membranes were hybridized overnight at 42° C., washed (twice with 2X SSC, 0.1% SDS; once with 0.1X SSC at 42° C. for 30 minutes), air dried, and exposed to autoradiography film at 70° C.

Dot Blot Analysis of Amplified Products

Seventy-five to eighty microliters of the amplified PCR reaction mixture were diluted with 200 microliters of TE buffer and blotted on to membranes using a dot blot vacuum manifold apparatus (BIO-DOT, Biorad Laboratories, Richmond, Calif.) according to the manufacture's instructions. Membranes were hybridized with the radiolabelled KSU-2 DNA probe.

Isolation and Purification of the PCR Product

Twenty-five microliters from each PCR reaction containing amplified product were loaded on to 1% agarose gels and electrophoresed at 100 V for 45 minutes. The gels were stained with ethidium bromide, and the amplification products were visualized by ultraviolet illumination. The amplification products were purified from the gel (PREPGENE, BioRad Laboratories, Richmond, Calif.), and stored at −20° C. Initial PCR reactions, 1 nanogram of purified KSU-2 was used as template, and the amplified products could be visualized on agarose gels as a single band at approximately 500 base pairs. Transfer and hybridization of the amplified products with KSU-2 confirmed that sequences within the amplified DNA were complementary to KSU-2 sequences.

5'TCTTCAACTCTTCCTATGGATCTAGAAAGAGTATGGCTGACACAGCAGTGAAAACTGCTAAGT (Sequence Id. no. 3)
CAGGTTACATGACTAGAAAACTTGTGGATGCTTCACAAGAAGTAGTAGTTAGATCCATAGACTGT
AATCCTAAGAAGGGAGTCTTAATAAGAGCTATTAAGGCTGAAGAGGTGACAGTATGGTTAAGAC
TCTTGAAGAGAGACTTAGATATAGATGTGCGTTTAAGGACATTGTATGTCCTCAAACAGGAGAAG
TACTGTGTGCTGAAGGAGAATACTTACTCCTAAGATAGCTAAGAAAATACAAGATCTTGGATTCG
AAGAAGTAGAAGTGAGAGGAGCATTTACTTGTGAACAAAAACCATGTGGTGTTTGTCAAAAATGT
TTCGGTTACGACCTTAAGACTAAGAAACCAGTTAAGGTCGGAACTGCTGTCGGAATAATTGCAGC
TCAATCAATTGGTGAGCCTGCAACACAACTTACCATGAG 3'.

In the 5' direction the amplification product is:

CTCATGGTAAGTTGTGTTGCAGGCTCACCAATTGATTGAGCTGCAATTATTCCGACAGCA (Sequence Id. no 4)
GTTCCGACCTTAACTGGTTTCTTAGTCTTAAGGTCGTAACCGAAACATTTTTGACAAACA
CCACATGGTTTTTGTTCACAAGTAAATGCTCCTCTCACTTCTACTTCTTCGAATCCAAGA
TCTTGTATTTTCTTAGCTATCTTAGGAGTAAGTATTCTCCTTCAGCACACAGTACTTCTC
CTGTTTGAGGACATACAATGTCCTTAAACGCACATCTATATCTAAGTCTCTCTTCAAGAG
TCTTAACCATACTGTCACTTCCCTCAGCCTTAATAGCTCTTATTAAGACTCCCTTCTTAG
GATTACAGTCTATGGATCTAACTACTACTTCTTGTGAAGCATCCACAAGTTTTCTAGTCA
TGTAACCTGACTTAGCAGTTTTCACTGCTGTGTCAGCCATACTCTTTCTAGATCCATAGG
AAGAGTTGAAGA.

The twenty oligonucleotide primers are shown in bold and are underlined.

The purified amplification product was subcloned in to pBluescript and sequenced using dideoxy chain termination method. See Sanger, supra. Amplification products to be used as probes were labeled by random priming (Oligolabeling kit, Pharmacia LKB Biotechnology, Piscataway, NJ) using [alpha-$^{32}$P]-dCTP(3000Ci/mM)-(DuPont/NEN Research Products, Boston, Mass.).

Restriction Endonuclease Digestion of KSU-2

Intact KSU-2 was digested with BamHI, and the products run on agarose gels, transferred to a membrane, and hybridized as previously described using [$^{32}$P]-labeled, purified 492 base pair PCR amplification product DNA as the probe. Specificity of the amplification product to the 2.9 Kb fragment of KSU-2 was confirmed by hybridizing the amplified DNA to a BamHI digest of KSU-2 DNA. The amplified product hybridized to both the intact KSU-2 and the 2.9 Kb fragment, but not to a 2.3 Kb fragment. Sequence analysis of the amplification product further confirmed the identity of the amplified DNA to a 492 base pair sequence of the 2.9 Kb fragment.

Sensitivity

The sensitivity of the *E. suis*-specific PCR was initially assessed using serial dilutions of KSU-2 DNA ($10^{-8}$ ng to 1 ng) as template for PCR. Following amplification, products were electrophoresed, transferred to membranes and hybridized with [$^{32}$P]-labelled KSU-2 probe. DNA extracted from pES was also used in sensitivity assays using dilutions of total genomic *E. suis* DNA (0.0045 ng to 900 ng). The dilutions served as template for PCR which followed by electrophoresis, transfer to membranes and hybridization as previously described. Successful amplification of KSU-2 DNA probe occurred when greater than 1 pg was used as template in the PCR reaction. *E. suis* specific amplification products were detectable in samples containing greater than 0.45 ng of pES (representing total *E. suis* genomic DNA).

Detection of *E. suis* Infection in a Splenectomized Pig

Preinfection blood samples were taken from a splenectomized pig, which was inoculated with *E. suis* organisms as previously described. Blood samples were taken daily until day ten postinfection when maximum parasitemia occurred. DNA was extracted from these samples as previously described and ten microliters of extracted DNA was used as a template for each PCR reaction. The amplification products were electrophoresed on 1% agarose gels, stained with ethidium bromide and visualized by ultraviolet transillumination. Transfer to membranes and hybridization with [$^{32}$P]-labelled KSU-2 probe was done as previously described.

In amplifications completed on blood samples taken sequentially from a splenectomized, *E. suis*-infected pig, no amplification product was present in the preinfected samples; however, a band of approximately 500 basepairs was present in the samples taken 24 hours postinfection and in subsequent samples tested.

Successful amplification of a 492 basepair fragment of the *E. suis* genome occurred when PCR amplifications were completed using KSU-2 as the original template. Sequence analysis and hybridization of the amplified fragment with BamHI-digested KSU-2 confirmed that the 492 base pair DNA was complementary to a sequence within the 2.9 Kb fragment of KSU-2 DNA. When PCR was performed on the DNA extracted from the blood of *E. suis*-infected pigs, a similarly sized fragment was produced that successfully hybridized to KSU-2. This confirmed specificity of the PCR product to KSU-2 and to *E. suis* DNA. Negative controls included blood from uninfected pigs and from cats. Neither of these samples resulted in detectable amplification products when used as templates in PCR.

Sensitivity studies indicated that the described PCR protocol is capable of detecting as little as 450 picograms of total *E. suis* genomic DNA. Estimated weights of rickettsial organisms range from approximately $1.0 \times 10^9$ daltons to $1.5 \times 10^9$ daltons. Kreier et al., *Bergey's Manual of Systematic Bacteriology*, vol. 1, ed. Krieg NR, pp. 698–729, Williams and Wilkins, Baltimore, Md. Using this range, 450 picograms of *E. suis* genomic DNA corresponds to approximately 5000 organisms.

The ability of the described PCR protocol to detect early *E. suis* infection in a splenectomized pig was demonstrated by the presence of a 492 base pair amplification product from 24 hour postinfection blood samples. This diagnostic method can be used for the diagnosis and pathogenetic study of eperythrozoonosis in pigs. The use of PCR as a diagnostic test to detect *E. suis* infection would allow accurate identification of infected animals within a herd and also epidemiologic studies to determine the prevalence and significance of *E. suis* infection among pigs.

EXAMPLE 1

KSU-2 Hybridization Assay Versus PCR

Splenectomized Pig Experiments

In experimental infections using splenectomized pigs, the eperythrozoon specific PCR/hybridization assay was able to detect *E. suis* earlier and in smaller blood volumes than the previous direct hybridizations with unamplified blood DNA. Similarly, in longitudinal experiments using nonsplenectomized pigs the *E. suis* PCR/hybridization assay was able to detect eperythrozoon DNA sequences within 24 hours post infection. These results are described in this example. Hybridization with the KSU-2 DNA probe on unamplified DNA from blood samples of splenectomized pigs infected with *E. suis* have been previously described. See Oberst et al., *Am. J. Vet. Res*, 51:1760–64 (1990). Briefly, three splenectomized pigs (A, B, and C) were inoculated intraperitoneally with 3.0 ml of *E. suis* infected blood, and another pig (D) was splenectomized and uninfected. Blood was collected in anticoagulant (EDTA) blood collection tubes from each pig prior to infecting and ensuing sampling dated postinfection (day 3,5,7,10,11 and 17) and stored at −20.0° C.

In experiments that monitored the parasitemia of splenectomized pigs using the KSU-2 DNA probe a specific radiographic signal indicative of the presence of *E. suis* DNA in the blood was found by day 7 postinfection in all splenectomized pigs tested. The DNA used in each dot blot well was equivalent to the total DNA from 100 microliters of whole blood collected that day and was extracted from a high salt solution (HSS). However, experiments using blood collected on the same day but with template DNA extracted by the quick boil method from frozen whole blood, showed that PCR/hybridizations were able to detect eperythrozoon DNA in infections earlier than direct hybridizations with unamplified blood DNA extracted from HSS.

Amplifying the equivalent of 10 microliters of blood DNA extracted by the quick boil method from splenectomized pig A collected on day 0 and days 3, 5, and 7 postinfection and then hybridized with KSU-2 DNA probe resulted in an intense radiographic signal on all collected dates. Splenectomized pigs B and C gave radiographic indications of the presence of *E. suis* sequences in amplified blood samples on day three post infection.

Nonsplenectomized Pig Experiments

Additionally, in other experiments, nonsplenectomized pigs "A" and "B" were bled on day 0, infected with *E. suis* and subsequently bled on days 1–16, 20, 22–26, 28–30 postinfection (pig "A" was also bled on day 30 postinfection). Blood DNA equivalent to 10 microliters of whole blood was amplified by PCR and the resulting products electrophoresed in agarose gels, stained with ethidium bromide, blotted by capillary action to the membrane and hybridized with KSU-2 DNA probe. Both pigs were splenectomized on day 22 postinfection. All blood samples were stored at −20.0° C.

In the nonsplenectomized pigs ("A" and "B") amplified DNA product (i.e. an approximately 490 base pair) was evident in blood from pig "A" in ethidium bromide stained gels within one day postinfection. Hybridization with PCR products from each blood sampling day from pig "A" confirmed the presence of *E. suis* on day one post infection. Hybridization signals for *E. suis* PCR product from pig "A" blood continued until day 22 when the pig was splenectomized.

Amplified DNA products were also evident in gels from nonsplenectomized pig "B". Hybridization of day 1 postinfection PCR products resulted in an intense radiographic signal with the KSU-2 DNA probe. Radiographic signals continued through day 22 postinfection, when the pig was splenectomized, and through the completion of the experiment on day 29 postinfection.

Example 2

PCR Analysis of Two Natural Outbreaks of Eperythrozoonosis

In the screening of blood samples in two natural outbreaks the presently described PCR assay was able to rapidly and specifically demonstrate two separate herds with eperythrozoonosis. The results indicate that pigs infected with E. suis from geographically distinct locations can be identified using eperythrozoon specific PCR hybridization assay.

Outbreak 1

History and pathology of an outbreak of eperythrozoonosis is described in the following section. Three pigs (605,606, and 697) were received alive (15lbs., 5-7 weeks old) at the Oklahoma Animal Disease Diagnostic Laboratory, Stillwater, Okla., and were euthanized by carbon dioxide gas and exsanguination. Pig 605 appeared "acutely ill," whereas pigs 606 and 607 were characterized as "chronic." The pigs originated in an Oklahoma farrowing operation of approximately 250 sows and piglets. A scouring problem was recognized approximately three weeks previously in nursing piglets in the farrowing barn. Scour material was characterized at that time as "yellow and greasy" by the referring veterinarian. When the pigs were transferred to a nursery the scour material changed to a "green" consistency and pigs began "wasting away".

At the time of submission approximately 65 pigs had been afflicted and twelve had died. Most of the pigs had been raised on the premises, but some gilts had been added to the farrowing operation five months previously. All sows had been vaccinated for leptospirosis and for colibacillosis, the exception being sows with sick litters.

Pig 605, the largest of the three pigs, had some yellow staining fecal material on the skin, hair of the tail, and perineum. Pigs 606 and 607 had green diarrheic fecal material. The tissues had an obvious paleness, and the blood was thin and watery. Overall, the skin of pig 605 had a yellow cast, but there was no distinct yellowness to the fascia and fat. Examination of the digestive tract gave gross evidence of diarrhea.

Pig 606 and 607 were essentially similar in most respects. Both had green diarrheic fecal material, rough haircoats, and marked bony prominences, and their blood was thin and watery.

Blood smears were negative for parasites for all three pigs. Blood samples submitted for E. suis DNA studies from pigs 605, 606 and 607 were mixed with a chaotropic salt solution (HSS) to inhibit degradation of nucleic acids and to preserve the DNA samples without refrigeration.

Eighteen days after the initial submission, new blood samples from pigs 606, 609 and 610 were submitted for evaluation.

Outbreak 2

The history of a second outbreak of eperythrozoonosis is described in the following section. An Oklahoma operation began having serious problems with sows and piglets in July and August of 1991. The pigs affected were sows that had been in contact with three out-of-state purebred gilts introduced to the herd in the spring. One of the gilts died during farrowing and the other two died after farrowing. Piglets from the sows were "stunted, poor-doers, appeared more susceptible to disease, and in general did not do well" and approximately ten died. Since the original problem, the herd had been given chlortetracyclines in the feed (100 g/ton) and wormed three times. Nine of the affected pigs were mixed with twenty other gilts, boars and barrows two weeks prior to bleeding. Seven of the 29 were randomly isolated and bled (November, 1991), as were two additional pigs in adjacent pens containing younger pigs. Blood samples submitted from these pigs (611-619) were stored at 4° C. and used in the DNA studies.

For all of pigs except 605-607, the whole blood DNA was extracted by a modified quick boil method. Briefly, 100 microliters of whole blood from each sample were combined with 200 microliters of sterile distilled water and heated to 100° C. for five minutes. The lysate was cooled briefly and phenol-chloroform extracted; then the DNA was ethanol precipitated. The DNA was suspended in 100 microliters of sterile water, quantitated ($A_{260}$-$A_{280}$), and stored at $-20°$ C.

Blood from pigs 605, 606 and 607 was collected in HSS, which has been previously described in unamplified hybridizations with the KSU-2 probe. See Oberst et al., Am. J. Vet. Res, 51:1760-64 (1990 hereby incorporated by reference). In PCR/hybridization assays, the equivalent of 100 microliters of whole blood was extracted from the original HSScontaining samples. Protein was precipitated from the lysate with 0.3X volumes of ethanol:chloroform:isoamyl alcohol (2.5:1:0:0.04), mixed for five minutes and then centrifuged at 14,000 X g for 15 minutes. The supernates were removed and the DNA was precipitated with ethanol. The DNA was pelleted and resuspended in 250 microliters of NET buffer (150 mM NaCl, 5 mM EDTA, and 50 mM Tris-HCl pH 7.5); extracted with phenol-chloroform; precipitated with ethanol; and resuspended in 100 microliter of NET buffer.

The amplification of E. suis was carried out as previously described. Initial samples involved blood from pigs 605, 606 and 607 collected in HSS, from which the DNA was subsequently extracted, amplified, dot blotted and hybridized with the KSU-2 DNA probe. Results of these hybridizations and comparisons with purified E. suis DNA and cat blood DNA indicated that E. suis DNA was present in pigs 605 and 606, but not pig 607. In subsequent blood samplings from this herd, DNA amplifications were completed on DNA recovered by the modified quick boil method. In the ensuing hybridizations with the KSU-2 DNA probe, the product of PCR of blood from pigs 608, 609, 610, and purified E. suis resulted in discernable hybridization signals, indicating the presence of E. suis DNA in the samples. With respect to the blood collected from pigs 611-619 distinct PCR/hybridization products were detected for pigs 611, 613, 614, 616, 617, 618, and 619, and a faint hybridization signal for pig 615 was observed. Pig 612 was judged to be negative when compared to purified E. suis (positive control) and cat blood DNA (negative control).

Although the invention has been described in terms of the specific embodiments many modifications and variations of the present invention are possible in light of the teachings. It is, therefore, to be understood that within the scope of the appended claims the invention may be practiced otherwise than as specifically described.

---

We claim:

1. A method of identifying early *Eperythrozoon suis* infection in pig blood comprising: isolating DNA from pig blood, contacting said DNA and with oligonucleotide primers consisting of the two single stranded oligonucleotide TCTTCAACTCTTCCTATGGA (SEQ ID NO: 1) and CTCATGGTAAGTTGTGTTGC (SEQ ID NO: 2), amplifying said DNA by polymerase chain reaction, and detecting an amplification product; wherein the presence of the amplification product indicates an early *Eperythrozoon suis* infection.

2. A synthetic oligonucleotide useful in detecting early *Eperythrozoon suis* infected blood by specifically priming an eperythrozoon specific polymerase chain reaction having the DNA sequence TCTTCAACTCTTCCTATGGA (SEQ ID NO: 1).

3. A synthetic oligonucleotide useful in detecting early *Eperythrozoon suis* infected blood by specifically priming an eperythrozoon specific polmerase chain reaction having the DNA sequence CTCATGGTAAGTTGTGTGTTGC (SEQ ID NO: 2).

4. A double stranded DNA amplification product having the DNA sequence set out in SEQ ID NO: 3 on one strand and SEQ ID NO: 4 on the other strand.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
     ( A ) LENGTH: 20 base pairs
     ( B ) TYPE: nucleic acid
     ( C ) STRANDEDNESS: unknown
     ( D ) TOPOLOGY: unknown ( i i ) MOLECULE TYPE: DNA (genomic)

( x i ) SEQUENCE DESCRIPTION: SEQ ID NO:1:

| TCTTCAACTC TTCCTATGGA | 20 |

( 2 ) INFORMATION FOR SEQ ID NO:2:

( i ) SEQUENCE CHARACTERISTICS:
     ( A ) LENGTH: 20 base pairs
     ( B ) TYPE: nucleic acid
     ( C ) STRANDEDNESS: unknown
     ( D ) TOPOLOGY: unknown ( i i ) MOLECULE TYPE: DNA (genomic)

( x i ) SEQUENCE DESCRIPTION: SEQ ID NO:2:

| CTCATGGTAA GTTGTGTTGC | 20 |

( 2 ) INFORMATION FOR SEQ ID NO:3:

( i ) SEQUENCE CHARACTERISTICS:
     ( A ) LENGTH: 492 base pairs
     ( B ) TYPE: nucleic acid
     ( C ) STRANDEDNESS: unknown
     ( D ) TOPOLOGY: unknown ( i i ) MOLECULE TYPE: DNA (genomic)

( x i ) SEQUENCE DESCRIPTION: SEQ ID NO:3:

| TCTTCAACTC | TTCCTATGGA | TCTAGAAAGA | GTATGGCTGA | CACAGCAGTG | AAAACTGCTA | 60 |
| AGTCAGGTTA | CATGACTAGA | AAACTTGTGG | ATGCTTCACA | AGAAGTAGTA | GTTAGATCCA | 120 |
| TAGACTGTAA | TCCTAAGAAG | GGAGTCTTAA | TAAGAGCTAT | TAAGGCTGAG | GAAGTGACA | 180 |
| GTATGGTTAA | GACTCTTGAA | GAGAGACTTA | GATATAGATG | TGCGTTTAAG | GACATTGTAT | 240 |
| GTCCTCAAAC | AGGAGAAGTA | CTGTGTGCTG | AAGGAGAATA | CTTACTCCTA | AGATAGCTAA | 300 |
| GAAAATACAA | GATCTTGGAT | TCGAAGAAGT | AGAAGTGAGA | GGAGCATTTA | CTTGTGAACA | 360 |
| AAAACCATGT | GGTGTTTGTC | AAAAATGTTT | CGGTTACGAC | CTTAAGACTA | AGAAACCAGT | 420 |
| TAAGGTCGGA | ACTGCTGTCG | GAATAATTGC | AGCTCAATCA | ATTGGTGAGC | CTGCAACACA | 480 |
| ACTTACCATG | AG | | | | | 492 |

( 2 ) INFORMATION FOR SEQ ID NO:4:

( i ) SEQUENCE CHARACTERISTICS:
     ( A ) LENGTH: 492 base pairs
     ( B ) TYPE: nucleic acid
     ( C ) STRANDEDNESS: unknown
     ( D ) TOPOLOGY: unknown ( i i ) MOLECULE TYPE: DNA (genomic)

( x i ) SEQUENCE DESCRIPTION: SEQ ID NO:4:

```
CTCATGGTAA GTTGTGTTGC AGGCTCACCA ATTGATTGAG CTGCAATTAT TCCGACAGCA    60
GTTCCGACCT TAACTGGTTT CTTAGTCTTA AGGTCGTAAC CGAAACATTT TTGACAAACA   120
CCACATGGTT TTTGTTCACA AGTAAATGCT CCTCTCACTT CTACTTCTTC GAATCCAAGA   180
TCTTGTATTT TCTTAGCTAT CTTAGGAGTA AGTATTCTCC TTCAGCACAC AGTACTTCTC   240
CTGTTTGAGG ACATACAATG TCCTTAAACG CACATCTATA TCTAAGTCTC TCTTCAAGAG   300
TCTTAACCAT ACTGTCACTT CCCTCAGCCT TAATAGCTCT TATTAAGACT CCCTTCTTAG   360
GATTACAGTC TATGGATCTA ACTACTACTT CTTGTGAAGC ATCCACAAGT TTTCTAGTCA   420
TGTAACCTGA CTTAGCAGTT TTCACTGCTG TGTCAGCCAT ACTCTTTCTA GATCCATAGG   480
AAGAGTTGAA GA                                                       492
```